US012600693B2

(12) United States Patent (10) Patent No.: US 12,600,693 B2
Kimura et al. (45) Date of Patent: Apr. 14, 2026

(54) METHOD FOR PRODUCING COMPOUND

(71) Applicant: NIPPON SHOKUBAI CO., LTD.,
Osaka (JP)

(72) Inventors: Hayato Kimura, Himeji (JP); Masashi Mukae, Himeji (JP); Takayuki Matsuda, Himeji (JP)

(73) Assignee: NIPPON SHOKUBAI CO., LTD.,
Osaka (JP)

( * ) Notice: Subject to any disclaimer, the term of this patent is extended or adjusted under 35 U.S.C. 154(b) by 488 days.

(21) Appl. No.: 18/025,527

(22) PCT Filed: Sep. 8, 2021

(86) PCT No.: PCT/JP2021/033038
§ 371 (c)(1),
(2) Date: Mar. 9, 2023

(87) PCT Pub. No.: WO2022/054842
PCT Pub. Date: Mar. 17, 2022

(65) Prior Publication Data
US 2024/0010598 A1 Jan. 11, 2024

(30) Foreign Application Priority Data

Sep. 11, 2020 (JP) ................................. 2020-153288

(51) Int. Cl.
*C07C 51/43* (2006.01)
(52) U.S. Cl.
CPC .................................... *C07C 51/43* (2013.01)
(58) Field of Classification Search
CPC ....... C07C 51/43; C07C 51/252; C07C 51/42;
C07C 57/04; B01D 9/0045; B01D 35/02
See application file for complete search history.

(56) References Cited

U.S. PATENT DOCUMENTS

2003/0060661 A1 3/2003 Eck et al.
2003/0175159 A1 9/2003 Heilek et al.
(Continued)

FOREIGN PATENT DOCUMENTS

CN 1422240 A 6/2003
CN 101497563 A 8/2009
(Continued)

OTHER PUBLICATIONS

Machine translation of JP-2006069959-A (Year: 2006).*
(Continued)

*Primary Examiner* — Deborah D Carr
(74) *Attorney, Agent, or Firm* — Dickinson Wright PLLC

(57) ABSTRACT

Provided is a method for obtaining high-quality products safely and stably. The present invention relates to a method for producing a compound, the method including feeding a slurry containing crystals of the compound to a hydraulic wash column; melting crystals in a crystal-containing circulation slurry discharged from the hydraulic wash column; discharging a mother liquor using a filter from the crystal-containing slurry in the hydraulic wash column; and introducing a liquid having a temperature equal to or higher than the temperature of the mother liquor immediately after being discharged in the mother liquor discharging step into a nozzle attached to the hydraulic wash column from outside the hydraulic wash column, the nozzle being other than a nozzle at a return port for a circulation liquid containing a melt obtained in the melting and a pipe that feeds the crystal-containing slurry to the hydraulic wash column.

17 Claims, 1 Drawing Sheet

(56) References Cited

U.S. PATENT DOCUMENTS

| | | | |
|---|---|---|---|
| 2004/0256319 A1 | 12/2004 | Hammon et al. | |
| 2005/0006299 A1* | 1/2005 | Heilek | B01D 9/004 |
| | | | 210/323.2 |
| 2007/0129572 A1 | 6/2007 | Shibusawa et al. | |
| 2010/0273970 A1 | 10/2010 | Koestner et al. | |
| 2011/0124834 A1 | 5/2011 | Heilek et al. | |
| 2011/0319661 A1 | 12/2011 | Sakamoto et al. | |
| 2019/0039987 A1 | 2/2019 | Kanaya et al. | |
| 2020/0181056 A1* | 6/2020 | Kase | C07C 51/43 |

FOREIGN PATENT DOCUMENTS

| | | | |
|---|---|---|---|
| CN | 102282120 A | 12/2011 | |
| CN | 102666464 A | 9/2012 | |
| CN | 109071402 A | 12/2018 | |
| CN | 110678440 A | 1/2020 | |
| DE | 102009045767 A1 | 8/2010 | |
| DE | 102010030279 A1 | 10/2010 | |
| JP | 11-123302 A | 5/1999 | |
| JP | H11-123302 A | 5/1999 | |
| JP | 2005-509010 A | 4/2005 | |
| JP | 2006069959 A * | 3/2006 | |
| JP | 2007-182437 A | 7/2007 | |
| JP | 2010-059107 A | 3/2010 | |
| JP | 2011-514311 A | 5/2011 | |
| JP | 2013-507427 A | 3/2013 | |
| WO | 2003/041832 A1 | 5/2003 | |
| WO | 2009/095111 A1 | 8/2009 | |
| WO | WO-2018216699 A1 * | 11/2018 | C07C 51/44 |

OTHER PUBLICATIONS

International Search Report dated Nov. 22, 2021, which issued in the corresponding PCT Patent Application No. PCT/JP2021/033038, including English translation.

* cited by examiner

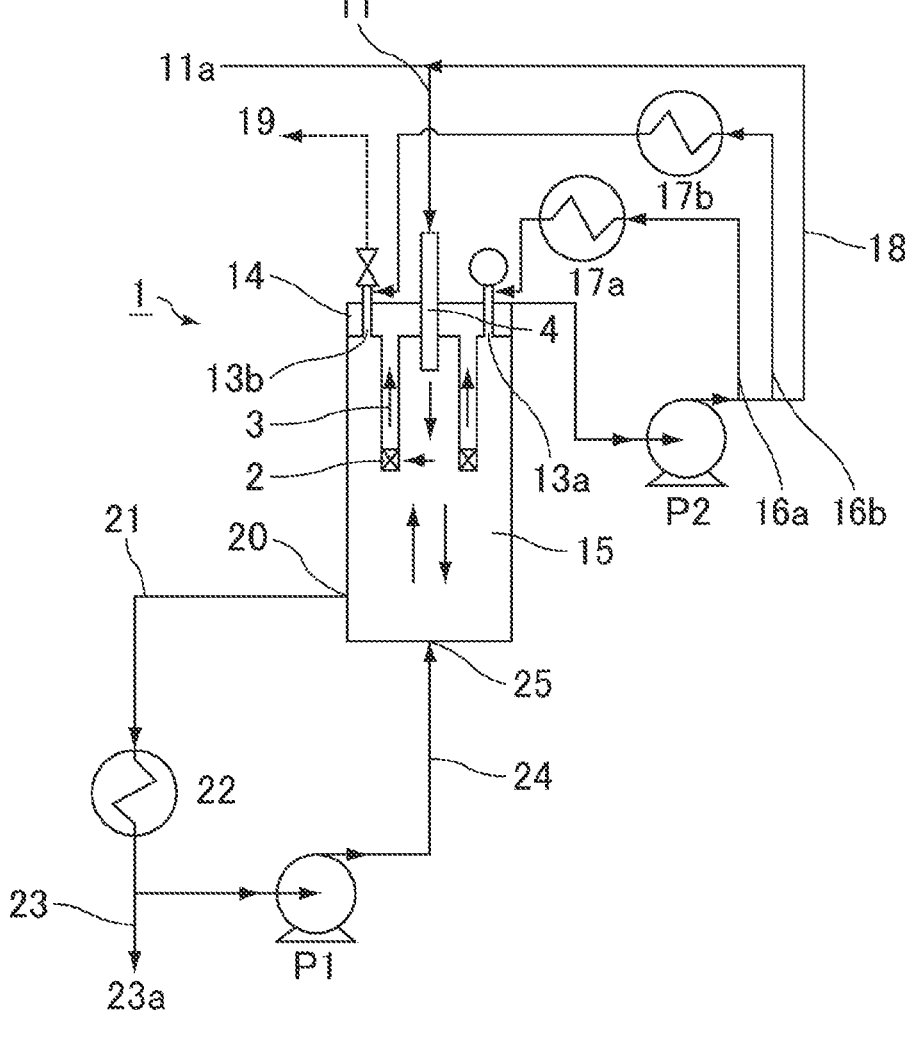

METHOD FOR PRODUCING COMPOUND

TECHNICAL FIELD

The present invention relates to methods for producing compounds. Specifically, the present invention relates to a method for producing a compound, a method for purifying a compound, and a purification apparatus.

BACKGROUND ART

Compounds, including easily polymerizable compounds such as (meth)acrylic acid, are widely used industrially as raw materials for resins, for example. Various studies have been made on better purification techniques for safe and stable production of high-quality compounds.

Industrially, many of crude compounds, which are compounds before purification, are purified through continuous purification processes. Disclosed is a method for producing acrylic acid including: collecting and crystallization purifying a gas containing acrylic acid obtained by catalytic oxidation of a raw material gas in gas phase; and returning acrylic acid obtained by decomposing a substance obtained by Michael addition of acrylic acid in a residual mother liquor to the collecting step, for example (see, for example, Patent Literature 1). In such a purification process, safe and stable operation of the apparatus is required.

In the purification process, a wash column such as a hydraulic wash column (HWC) may be used. Patent Literatures 2 and 3 disclose purification methods using conventional wash columns.

CITATION LIST

Patent Literature

Patent Literature 1: JP 2007-182437 A
Patent Literature 2: JP 2013-507427 T
Patent Literature 3: JP 2005-509010 T

SUMMARY OF INVENTION

Technical Problem

As described above, better purification techniques for producing compounds have been desired to obtain high-quality products (compounds) with apparatuses under safe and stable operation. The present invention has been made in view of the above-mentioned current state of the art, and aims to provide a method for obtaining high-quality products safely and stably.

Solution to Problem

The present inventors have studied methods for producing compounds, and focused on using a hydraulic wash column with high washing efficiency in the purification of compounds. They found that a mother liquor is discharged using a filter from a crystal-containing slurry in the hydraulic wash column, and is collected, and a liquid having a temperature higher than the temperature of the mother liquor immediately after being discharged is passed through a nozzle attached to the hydraulic wash column, so that freezing can be prevented and the apparatus can be operated more safely and stably. Thereby, the present invention has been achieved.

That is, the present invention relates to a method for producing a compound, the method including: a step of feeding a slurry containing crystals of the compound to a hydraulic wash column; a step of melting crystals in a crystal-containing circulation slurry discharged from the hydraulic wash column; a step of discharging a mother liquor using a filter from the crystal-containing slurry in the hydraulic wash column; and a step of introducing a liquid having a temperature equal to or higher than the temperature of the mother liquor immediately after being discharged in the mother liquor discharging step into a nozzle attached to the hydraulic wash column from outside the hydraulic wash column, the nozzle being other than a nozzle at a return port for a circulation liquid containing a melt obtained in the melting step and a pipe that feeds the crystal-containing slurry to the hydraulic wash column.

Patent Literatures 2 and 3 neither describe nor suggest the invention relating to prevention of freezing of the liquid in and around a nozzle attached to the hydraulic wash column. Simply thermally insulating an area where instrumentation equipment is attached (the connection between an inner portion and an outer portion of the instrumentation equipment attached to the hydraulic wash column, with a nozzle being usually attached to the connection) with a jacket or an indirect trace system fails to prevent or reduce stagnation of the liquid in and around the nozzle at the area where the instrumentation equipment is attached and fails to sufficiently prevent freezing of the liquid.

Advantageous Effects of Invention

The purification apparatus of the present invention can provide a high-quality product safely and stably.

BRIEF DESCRIPTION OF DRAWINGS

FIG. 1 is an exemplary schematic diagram of the state of use of the purification apparatus of the present invention.

DESCRIPTION OF EMBODIMENTS

The present invention will be described in detail below.

It should be noted that combinations of two or more of the preferred features of the present invention described below are also preferred embodiments of the present invention.

The following first describes a method for producing a compound of the present invention, followed by descriptions of a method for purifying a compound of the present invention and a purification apparatus of the present invention in this order.

(Method for Producing a Compound of the Present Invention)

The present invention relates to a method for producing a compound, the method including: a step of feeding a slurry containing crystals of the compound to a hydraulic wash column; a step of melting crystals in a crystal-containing circulation slurry discharged from the hydraulic wash column; a step of discharging a mother liquor using a filter from the crystal-containing slurry in the hydraulic wash column; and a step of introducing a liquid having a temperature equal to or higher than the temperature of the mother liquor immediately after being discharged in the mother liquor discharging step into a nozzle attached to the hydraulic wash column from outside the hydraulic wash column, the nozzle being other than a nozzle at a return port for a circulation liquid containing a melt obtained in the melting step and a pipe that feeds the crystal-containing slurry to the hydraulic wash column.

Preferably, in the method for producing a compound of the present invention, the nozzle attached to the hydraulic wash column is at least one selected from the group consisting of an instrumentation nozzle, a sampling nozzle, a pressure control valve nozzle, a pipe insert nozzle, and an emergency injection nozzle.

An instrumentation nozzle, when frozen and clogged, may lead to a risk of erroneous indication by instruments, resulting in an unintended dangerous operating state, for example. Also, a sampling nozzle and the like, when frozen and clogged, may lead to a risk that the internal state cannot be accurately grasped, failing to control the quality and the like of the product (compound) to be obtained. Also, a pressure control valve nozzle and an emergency injection nozzle, when frozen and clogged, may lead to a risk that they may not play a role as safety devices in an emergency. Each nozzle will be described in detail below.

The method for producing a compound of the present invention can sufficiently prevent freezing and clogging of various nozzles. Sufficiently preventing freezing and clogging can achieve a clear grasp of the internal state (e.g., temperature, pressure) of the hydraulic wash column and a safer operation.

Basically, an object to be purified is subjected to the feeding step and the melting step in this order among the above steps. For example, as shown in FIG. 1, a crystal-containing slurry 11a is fed into a crystallization chamber 15 of a hydraulic wash column 1 through a feed line 11 and a pipe 4; a crystal-containing circulation slurry is discharged through a circulation slurry discharging port 20 at the bottom of the hydraulic wash column 1 and passes through a discharging line 21 that connects the circulation slurry discharging port 20 and a melting unit 22; and the crystals in the circulation slurry are melted in the unit 22. At least a portion of a circulation liquid containing the melt obtained by melting the crystals in the melting unit 22 passes through a product discharging line 23 and is discharged from the purification apparatus as a product 23a. The rest of the circulation liquid may be returned into the hydraulic wash column 1 through a return line 24 that connects the melting unit 22 and a return port 25. The crystal-containing slurry fed into the crystallization chamber 15 is filtered using a filter 2, and a mother liquor (filtrate) is discharged using a pipe 3 that is connected to the filter 2, and is collected in a mother liquor collection chamber 14. Thereafter, the mother liquor can be collected and recycled. The following first describes a step of introducing a liquid having a temperature equal to or higher than the temperature of the mother liquor immediately after being discharged into a nozzle attached to the hydraulic wash column, followed by descriptions of the feeding step, the melting step, the mother liquor discharging step, and other steps in this order. In a continuous purification process, the steps are usually performed simultaneously in the view of the whole purification apparatus.

Herein, the term "compound" refers to a compound obtained by the production method of the present invention, and does not refer to raw materials, by-products, and solvents in the production method of the present invention. The term "compound" may also be referred to as a "target compound" or a "target object".

Introducing Step

The method for producing a compound of the present invention includes a step of introducing a liquid having a temperature equal to or higher than the temperature of the mother liquor immediately after being discharged in the mother liquor discharging step into a nozzle attached to the hydraulic wash column from outside the hydraulic wash column, the nozzle being other than a nozzle at a return port for a circulation liquid containing a melt obtained in the melting step and a pipe that feeds the crystal-containing slurry to the hydraulic wash column.

According to the method for producing a compound of the present invention, stagnation of the liquid in and around a nozzle attached to the hydraulic wash column can be prevented or reduced and freezing and clogging thereof can be sufficiently prevented by introducing a liquid having a temperature equal to or higher than the temperature of the mother liquor immediately after being discharged in the mother liquor discharging step into the nozzle.

The introducing step is, in other words, a step of introducing a liquid having a temperature equal to or higher than the temperature of the mother liquor into the hydraulic wash column through a nozzle attached to the hydraulic wash column.

The temperature of the liquid having a temperature equal to or higher than the temperature of the mother liquor is preferably higher than the temperature of the mother liquor by 1° C. or more, more preferably by 2° C. or more, even more preferably by 3° C. or more, particularly preferably by 5° C. or more.

The temperature of the liquid having a temperature equal to or higher than the temperature of the mother liquor is preferably higher than the temperature of the mother liquor by 40° C. or less, more preferably by 35° C. or less, even more preferably by 30° C. or less, particularly preferably by 20° C. or less. In other words, the temperature of the liquid having a temperature equal to or higher than the temperature of the mother liquor is higher than the temperature of the mother liquor, and the difference therebetween is preferably 40° C. or less, more preferably 35° C. or less, even more preferably 30° C. or less, particularly preferably 20° C. or less.

When the temperature of the liquid to be introduced into a nozzle attached to the hydraulic wash column is lower than the temperature of the mother liquor, the effects of the present invention cannot be obtained. When the temperature of the liquid to be introduced into a nozzle is higher than the temperature of the mother liquor by more than 40° C., the operating conditions may be affected, e.g., crystals in the hydraulic wash column may melt.

The temperature of the liquid having a temperature equal to or higher than the temperature of the mother liquor can be set to an appropriate temperature according to the melting point of the compound, which may be within the range of 10° C. to 100° C., for example.

For example, when the compound is (meth)acrylic acid, the temperature of the liquid having a temperature equal to or higher than the temperature of the mother liquor is preferably 5° C. or higher, more preferably 10° C. or higher.

The temperature of the liquid is preferably 50° C. or lower, more preferably 40° C. or lower.

The temperature of the mother liquor can be appropriately adjusted within the range of 0° C. to 80° C.

For example, when the compound is (meth)acrylic acid, the temperature of the mother liquor is preferably 5° C. to 13° C., more preferably 7° C. to 11° C.

The temperature or the like of the liquid having a temperature equal to or higher than the temperature of the mother liquor is determined by measuring the temperature or the like of the liquid immediately before being introduced into a nozzle attached to the hydraulic wash column. The temperature or the like of the mother liquor immediately after being discharged in the mother liquor discharging step is determined by measuring the temperature or the like of the mother liquor in the pipe connected to the filter.

Preferably, in the method for producing a compound of the present invention, the liquid having a temperature equal to or higher than the temperature of the mother liquor contains at least one of the compound or water.

The content of the compound in the liquid having a temperature equal to or higher than the temperature of the mother liquor is preferably 85% by mass or more, more preferably 88% by mass or more, still more preferably 90% by mass or more.

The content of the compound in the liquid having a temperature equal to or higher than the temperature of the mother liquor is preferably 99% by mass or less, more preferably 98% by mass or less, still more preferably 97% by mass or less.

The liquid having a temperature equal to or higher than the temperature of the mother liquor may be introduced in any amount into a nozzle attached to the hydraulic wash column. The amount is, for example, $3 \times 10^1$ to $1 \times 10^3$ kg/h per nozzle in an industrial-scale hydraulic wash column.

As described above, preferably, in the method for producing a compound of the present invention, the nozzle attached to the hydraulic wash column is at least one selected from the group consisting of an instrumentation nozzle, a sampling nozzle, a pressure control valve nozzle, a pipe insert nozzle, and an emergency injection nozzle.

The instrumentation nozzle is configured to attach instrumentation instruments such as a thermometer (e.g., a multipoint thermometer), a pressure gauge, or an interface gauge (e.g., an optical interface gauge) to the hydraulic wash column.

The sampling nozzle is configured to sample the slurry or the like in the hydraulic wash column.

The pressure control valve nozzle is a nozzle to which a valve capable of controlling the pressure in the hydraulic wash column is attached. Examples of the valve include a valve that automatically or manually releases and controls the pressure, when rising, in the hydraulic wash column, a safety valve, and a valve through which the system is released to the atmosphere when the liquid in the hydraulic wash column is discharged.

The emergency injection nozzle is configured to inject a polymerization inhibitor, a stabilizer, a solvent, or the like from the outside when abnormal polymerization or the like occurs in the hydraulic wash column. The emergency injection nozzle is, in other words, a nozzle for injecting an additive and/or a solvent.

The pipe insert nozzle is used to insert a pipe that transports the slurry or the like into the hydraulic wash column and has an inner diameter larger than the outer diameter of the pipe.

Preferably, in the method for producing a compound of the present invention, the liquid having a temperature equal to or higher than the temperature of the mother liquor contains at least a portion of the mother liquor discharged in the mother liquor discharging step.

For example, the liquid having a temperature equal to or higher than the temperature of the mother liquor preferably contains 70% by mass or more, more preferably 80% by mass or more of the mother liquor discharged in the mother liquor discharging step. Particularly preferably, the mother liquor itself (100% by mass) is used as the liquid.

Preferably, in the method for producing a compound of the present invention, the liquid having a temperature equal to or higher than the temperature of the mother liquor contains at least a portion of the mother liquor discharged in the mother liquor discharging step, the portion of the mother liquor having been heated.

The heating temperature may be set at an appropriate temperature according to the melting point of the compound, and can be appropriately adjusted within the range of 10° C. to 100° C., for example.

For example, when the compound is (meth)acrylic acid, the heating temperature is preferably 15° C. or higher, more preferably 18° C. or higher. The heating temperature is preferably 50° C. or lower, more preferably 40° C. or lower.

The heating temperature is the temperature in the heater. When the heating is performed using a heating medium, the heating temperature is the temperature of the heating medium.

The heating duration may be set at an appropriate duration according to the melting point of the compound.

As shown in FIG. 1, at least a portion of the mother liquor discharged in the mother liquor discharging step is transported through mother liquor transfer lines 16a and 16b, and is heated with heaters 17a and 17b provided in the mother liquor transfer lines 16a and 16b, respectively. Thereby, the liquid having a temperature equal to or higher than the temperature of the mother liquor can be easily obtained.

The effects of the present invention are significantly achieved when in the method for producing a compound of the present invention, the nozzle attached to the hydraulic wash column penetrates a mother liquor collection chamber in which the mother liquor discharged in the mother liquor discharging step is collected, and is connected to a crystallization chamber to which the crystal-containing slurry in the hydraulic wash column is fed.

The mother liquor collection chamber is usually provided on the top of the crystallization chamber. When the nozzle attached to the hydraulic wash column penetrates a mother liquor collection chamber in which the mother liquor discharged in the mother liquor discharging step is collected, and is connected to a crystallization chamber to which the crystal-containing slurry in the hydraulic wash column is fed, thermally insulating the nozzle penetrating the mother liquor collection chamber or controlling the temperature thereof is difficult. Thus, the liquid in and around the nozzle tends to stagnate and freeze. According to embodiments of the present invention, stagnation of the liquid in and around the nozzle can be prevented, freezing thereof is sufficiently prevented, and thus, a compound can be produced stably.

The mother liquor collection chamber is a part (chamber) in which the mother liquor discharged in the mother liquor discharging step is collected.

When the hydraulic wash column includes the mother liquor collection chamber, the part (chamber) in the hydraulic wash column to which the slurry containing crystals of the compound is fed is also called a crystallization chamber. In this case, a pipe that feeds the crystal-containing slurry to the hydraulic wash column, described below, is, in other words, a pipe that feeds the crystal-containing slurry to the crystallization chamber of the hydraulic wash column.

In the introducing step, for example, as shown in FIG. 1, the crystal-containing slurry in the crystallization chamber 15 of the hydraulic wash column 1 is filtered using the filter 2; a mother liquor (filtrate) is discharged using the pipe 3 that is connected to the filter 2 and collected in the mother liquor collection chamber 14; and a portion of the mother liquor is transported through the mother liquor transport lines 16a and 16b, heated with the heaters 17a and 17b, and introduced into the nozzles 13a and 13b. In FIG. 1, the nozzle 13a is an instrumentation nozzle and the nozzle 13b is a pressure control valve nozzle. The pressure control valve nozzle is connected to a pressure control line 19. The pressure control line 19 is, for example, a line through which the mother liquor in the column is discharged when an openable pressure control valve opens in conjunction with a pressure gauge for controlling the internal pressure. The remaining mother liquor can be transported through a line 18, mixed with the crystal-containing slurry 11a, and fed to the hydraulic wash column (herein, the crystal-containing slurry encompasses a mixture of the crystal-containing slurry 11a and the remaining mother liquor).

Feeding Step

In the feeding step, the slurry containing crystals of the compound is fed to the hydraulic wash column. The crystal-containing slurry is a suspension of crystals of the compound and a mother liquor. In other words, the liquid portion of the slurry containing crystals of the compound to be fed to the hydraulic wash column is the mother liquor. The crystal-containing slurry can be obtained by generating crystals in a compound-containing solution (e.g., a (meth) acrylic acid aqueous solution or a crude (meth)acrylic acid solution) as described later. The compound-containing solution may be prepared in-house or procured from outside sources. The compound-containing solution encompasses a crude compound.

The mass percentage of the crystals in the crystal-containing slurry to be fed to the hydraulic wash column is preferably 1% by mass or more, more preferably 3% by mass or more, still more preferably 5% by mass or more.

The mass percentage of the crystals is preferably 50% by mass or less, more preferably 40% by mass or less, still more preferably 30% by mass or less, particularly preferably 20% by mass or less.

Herein, the expression "crystal-containing slurry to be fed to the hydraulic wash column" refers to the crystal-containing slurry immediately before being fed to the hydraulic wash column, and for example, refers to a crystal-containing slurry in a pipe that feeds a crystal-containing slurry to the hydraulic wash column.

Preferably, in the crystal-containing slurry to be fed to the hydraulic wash column, the mother liquor contains the compound. Examples of the mother liquor include the above-described compound and an aqueous solution of the compound. The mother liquor usually contains impurities other than the compound and water.

In the method for producing a compound of the present invention, the purity (mass percentage) of the compound in the mother liquor in the crystal-containing slurry to be fed to the hydraulic wash column is preferably 97% by mass or less.

More preferably, the mass percentage of the compound in the mother liquor is 96% by mass or less.

The mass percentage of the compound in the mother liquor is preferably 85% by mass or more, more preferably 88% by mass or more, still more preferably 90% by mass or more.

In the production method of the present invention, the compound preferably has a melting point of 0° C. to 80° C., more preferably 1° C. to 50° C., still more preferably 3° C. to 40° C., particularly preferably 5° C. to 20° C.

The compound is preferably an easily polymerizable compound having a reactive double bond.

In particular, in the production method of the present invention, the compound is more preferably an unsaturated carboxylic acid, still more preferably (meth)acrylic acid, particularly preferably acrylic acid. Herein, the term (meth) acrylic acid refers to acrylic acid and/or methacrylic acid.

The mass percentage of water in the mother liquor is preferably 0.1% by mass or more, more preferably 0.5% by mass or more, still more preferably 1% by mass or more.

The mass percentage of water in the mother liquor is preferably 8% by mass or less, more preferably 6% by mass or less, still more preferably 4% by mass or less.

The mass percentage of impurities other than the compound and water in the mother liquor is preferably 0.1% by mass or more, more preferably 0.4% by mass or more, still more preferably 0.8% by mass or more.

The mass percentage of impurities other than the compound and water in the mother liquor is preferably 8% by mass or less, more preferably 6% by mass or less, still more preferably 4% by mass or less.

When the compound is (meth)acrylic acid, the impurities other than the compound and water may include acetic acid and furfural, for example.

In this case, the mass percentage of acetic acid in the mother liquor is preferably 0.1% by mass or more, more preferably 0.3% by mass or more, still more preferably 0.7% by mass or more.

The mass percentage of acetic acid in the mother liquor is preferably 8% by mass or less, more preferably 6% by mass or less, still more preferably 4% by mass or less.

When the compound is (meth)acrylic acid, the mass percentage of furfural in the mother liquor is more preferably 0.01% by mass or more, more preferably 0.05% by mass or more, still more preferably 0.1% by mass or more.

The mass percentage of furfural in the mother liquor is preferably 2% by mass or less, more preferably 1% by mass or less, still more preferably 0.5% by mass or less.

In the feeding step, the crystal-containing slurry may be fed at any feed rate. For example, the feed rate is $0.2 \times 10^3$ to $4.0 \times 10^5$ kg/h in an industrial-scale hydraulic wash column.

In the feeding step, the feed temperature of the crystal-containing slurry can be appropriately selected according to the melting point of the compound or the like. For example, the feed temperature can be appropriately adjusted within the range of 0° C. to 80° C.

For example, when the compound is (meth)acrylic acid, the feed temperature of the crystal-containing slurry is preferably 5° C. to 13° C., more preferably 6° C. to 12° C.

The feed temperature of the crystal-containing slurry is the temperature of the mother liquor in the crystal-containing slurry immediately before being fed to the hydraulic wash column.

Melting Step

In the melting step, the crystals in the crystal-containing circulation slurry discharged from the hydraulic wash column are melted.

The crystals originate from a crystal bed formed at a lower part of the hydraulic wash column. The crystals can be discharged using the below-described mechanism that discharges the crystals from the crystal bed in the hydraulic wash column.

The crystals are usually discharged together with the circulation liquid, i.e., the crystals are discharged in the form of a crystal-containing circulation slurry. This circulation slurry is subjected to the melting step.

The circulation liquid is circulated as follows: the circulation liquid is discharged in the form of crystal-containing circulation slurry from the hydraulic wash column; and a portion of the circulation liquid containing the melt obtained in the melting step is returned to the hydraulic wash column and passes through the hydraulic wash column for circulation. In other words, the circulation liquid flows in a circulation path that passes through the hydraulic wash column. Herein, the liquid component in the circulation slurry flowing in the circulation path is also referred to as a circulation liquid.

Here, the circulation slurry is a suspension of crystals of the compound and the circulation liquid, and flows in the circulation path.

The mass percentage of the crystals in the crystal-containing circulation slurry discharged from the hydraulic wash column is preferably 0.5% by mass or more, more preferably 1% by mass or more, still more preferably 3% by mass or more, particularly preferably 5% by mass or more.

The mass percentage of the crystals is preferably 40% by mass or less, more preferably 30% by mass or less, still more preferably 20% by mass or less, particularly preferably 10% by mass or less.

Herein, the crystal-containing circulation slurry discharged from the hydraulic wash column refers to the crystal-containing circulation slurry immediately after being discharged from the hydraulic wash column, and, for example, refers to the crystal-containing circulation slurry in the discharging line (pipe) that connects the circulation slurry discharging port and the melting unit.

In the discharging line that connects the discharging port for crystals in the hydraulic wash column and the melting unit and in the return line that connects the melting unit and the return port of the hydraulic wash column, the circulation slurry or the circulation liquid containing the melt circulates. Herein, the circulation path is also referred to as a melt loop.

The crystal-containing circulation slurry is discharged from the hydraulic wash column at a discharging rate of $2 \times 10^3$ to $5 \times 10^5$ kg/h in an industrial-scale hydraulic wash column, for example, but is not limited thereto.

The discharged crystals can be melted using a heater. Examples of the heater include those having a structure that efficiently transfers heat to the crystal-containing slurry, such as a vertical multitubular heat exchanger, a horizontal multitubular heat exchanger, a double pipe heat exchanger, a spiral heat exchanger, a plate heat exchanger, or an electric heater. Preferably, the heater is provided in the melt loop and the circulation slurry and the circulation liquid after the melting step are circulated in the forced circulation system in which the circulation slurry is circulated by a pump provided in the melt loop.

The heating temperature in the melting step may be set to an appropriate temperature according to the melting point of the compound, and can be appropriately adjusted within the range of 10° C. to 100° C., for example.

For example, when the compound is (meth)acrylic acid, the heating temperature in the melting step is preferably or higher, more preferably 18° C. or higher. The heating temperature is preferably 50° C. or lower, more preferably 40° C. or lower.

When the heating is performed by feeding a heating medium to the melting unit, the heating temperature in the melting step is the feed temperature of the heating medium.

The temperature of the circulation liquid containing the melt at the outlet of the melting step (the melting unit) is preferably set to a temperature 1° C. to 10° C. higher than the melting point of the circulation liquid containing the melt obtained in the melting step (e.g., the circulation liquid containing the melt obtained after the crystal-containing slurry passes through the heat exchanger or the like and the crystals are melted).

The melting time in the melting step may be appropriately selected to the extent that the crystals are sufficiently melted.

Mother Liquor Discharging Step

The production method of the present invention includes a step of discharging a mother liquor using a filter from the crystal-containing slurry in the hydraulic wash column. For example, the production method of the present invention preferably includes a step of discharging a mother liquor, the step including filtering the crystal-containing slurry in the hydraulic wash column using a filter and discharging the mother liquor through a pipe connected to the filter. Preferably, in the mother liquor discharging step, a portion of the washing liquid described below is discharged together with the mother liquor. Thus, the discharged mother liquor preferably contains a portion of the washing liquid.

The discharged mother liquor can be recycled and reused. For example, the discharged mother liquor may be heated, and then may be used as a liquid having a temperature equal to or higher than the temperature of the mother liquor in the introducing step. Also, for example, reuse of the discharged mother liquor at least as a portion of the crystal-containing slurry to be fed to the hydraulic wash column can provide a compound with further improved quality.

When the density of the crystals is higher than that of the mother liquor, the mother liquor in the slurry fed in the feeding step flows downward from the top, runs into the washing liquid flowing upward from the bottom, and is pushed back. Thereby, the mother liquor is discharged through the filter.

The filter may be made of any material and may be made of, for example, metal such as stainless steel or resin such as polytetrafluoroethylene (PTFE), polyetheretherketone (PEEK), a tetrafluoroethylene-perfluoroalkylvinyl ether copolymer (PFA), or polyetherketone (PEK), with the latter being preferred. The pipe may be made of any material and is preferably made of metal or an alloy.

The mother liquor discharged in the mother liquor discharging step usually contains the compound. Examples of the mother liquor include a melt of the compound and an aqueous solution of the compound. The mother liquor usually contains impurities other than water.

The mother liquor discharged in the mother liquor discharging step refers to the mother liquor immediately after passing through the filter in the mother liquor discharging step.

The mother liquor discharging step can be appropriately performed using a pump or the like.

Returning Step

The production method of the present invention preferably includes a step of returning a portion of the circulation liquid containing the melt obtained in the melting step to the hydraulic wash column.

The circulation liquid contains the melt obtained in the melting step. In other words, the crystals in the discharged circulation slurry are melted to be a melt, so that the suspended circulation slurry becomes a non-suspended circulation liquid.

The melt obtained in the melting step refers to a liquid obtained by melting the crystals in the circulation slurry discharged from the hydraulic wash column in the melting step. The melt does not include those derived from the circulation liquid (liquid components) in the circulation slurry.

A portion of the circulation liquid containing the melt obtained in the melting step is returned to the hydraulic wash column, and a portion of the returned circulation liquid is used as a washing liquid for crystals in the hydraulic wash column.

The washing liquid is a portion of the circulation liquid that is returned to the hydraulic wash column. After returning to the hydraulic wash column, the portion of the circulation liquid is not discharged through the discharging port of the hydraulic wash column and is not recirculated in the circulation path, but, for example, flows countercurrent (preferably in an upward direction) to the conveying direction of the crystals through gaps between crystals of a crystal bed in the hydraulic wash column, thereby washing the crystals in the hydraulic wash column.

In an industrial-scale hydraulic wash column, in discharging a product accompanying the returning step, the product is discharged at a rate of 5 kg/h to $4.0 \times 10^4$ kg/h.

In the production method of the present invention, an outer wall surface of the hydraulic wash column may be heated by a heating medium or the like, and the temperature of the heating medium used for heating is appropriately set according to a substance to be treated, that is, a target compound.

The heating medium may be any liquid or gas, and examples include water, antifreeze, a methanol water mixture (an aqueous methanol solution), and gas. The heating medium may be appropriately selected in consideration of the freezing point of the compound to be purified and the like.

Freezing can be sufficiently prevented by heating the outer wall surface of the hydraulic wash column, leading to stable production of the compound.

The heating may be performed by heating part of the hydraulic wash column with a heating medium or the like. Preferably, substantially the entire hydraulic wash column is heated (jacket heating).

During operation, the inside of the hydraulic wash column is basically under pressure. The pressure is preferably within the range of 0.05 to 1.0 MPa.

Step of Preparing Crystal-Containing Slurry

The production method of the present invention preferably further includes a step of preparing a slurry containing crystals of a compound from a compound-containing solution.

The compound-containing solution can be prepared by collecting the gas of a compound, which is a reaction product obtained by a reactor, in an absorption tower, for example. The compound-containing solution encompasses a crude compound obtained by purifying the collected compound. The compound-containing solution is not limited to one synthesized in-house, and may be one procured from outside sources.

The compound-containing solution is cooled, for example, and thereby the slurry containing crystals of the compound can be obtained.

The compound-containing solution contains impurities other than the compound and water.

In the production method of the present invention, the compound-containing solution is preferably a (meth)acrylic acid aqueous solution or a crude (meth)acrylic acid solution.

The (meth)acrylic acid aqueous solution refers to a solution in which (meth)acrylic acid is dissolved in water. The crude (meth)acrylic acid solution is a solution composed of (meth)acrylic acid and containing impurities such as by-products produced during the production of the (meth)acrylic acid.

Examples of the impurities include acids such as propionic acid, acetic acid, maleic acid, benzoic acid, and acrylic acid dimers; aldehydes such as acrolein, furfural, formaldehyde, and glyoxal; acetone; methyl isobutyl ketone; toluene; and protoanemonin.

Step of Preparing Compound-Containing Solution

The production method of the present invention preferably further includes a step of preparing the compound-containing solution from a raw material.

The step of preparing the compound-containing solution may be any step that can provide the compound-containing solution. When the compound is (meth)acrylic acid, the step can be suitably carried out by synthesizing acrylic acid, collecting the acrylic acid, and the like, as described in JP 2007-182437 A (Patent Literature 1), for example.

In the method for producing a compound of the present invention, the raw material is preferably at least one selected from the group consisting of propane, propylene, acrolein, isobutene, methacrolein, acetic acid, lactic acid, isopropanol, 1,3-propanediol, glycerol, and 3-hydroxypropionic acid. The (meth)acrylic acid and/or the raw material may also be bio-based (meth)acrylic acids derived from renewable raw materials.

In the step of preparing the compound-containing solution, impurities such as by-products are basically generated. Although, for example, when the compound is (meth)acrylic acid, the impurities generated include water; acids such as propionic acid, acetic acid, maleic acid, benzoic acid, and acrylic acid dimers; aldehydes such as acrolein, furfural, formaldehyde, and glyoxal; acetone; methyl isobutyl ketone; toluene; and protoanemonin, purification or the like using the hydraulic wash column in the production method of the present invention can provide a high-quality product safely and stably.

Method for Purifying Compound

The present invention also relates to a method for purifying a compound, the method including: a step of feeding a slurry containing crystals of the compound to a hydraulic wash column; a step of melting crystals in a crystal-containing circulation slurry discharged from the hydraulic wash column; a step of discharging a mother liquor using a filter from the crystal-containing slurry in the hydraulic wash column; and a step of introducing a liquid having a temperature equal to or higher than the temperature of the mother liquor immediately after being discharged in the mother liquor discharging step into a nozzle attached to the hydraulic wash column from outside the hydraulic wash column, the nozzle being other than a nozzle at a return port for a circulation liquid containing a melt obtained in the melting step and a pipe that feeds the crystal-containing slurry to the hydraulic wash column.

The purification method of the present invention can safely and stably purify the crystal-containing slurry.

Preferred embodiments of the purification method of the present invention are the same as the preferred embodiments of the production method of the present invention described above.

Purification Apparatus

The present invention also relates to a purification apparatus that purifies crystals, the purification apparatus including: a hydraulic wash column that includes a discharging port for a crystal-containing circulation slurry and a return port for a circulation liquid containing a melt of discharged crystals; a pipe that feeds a crystal-containing slurry to the hydraulic wash column; a filter that discharges a mother liquor from the crystal-containing slurry in the hydraulic wash column; a pipe that is connected to the filter and transports the mother liquor; a nozzle at an introduction port that introduces a liquid to the hydraulic wash column, the nozzle being other than a nozzle at the return port and a pipe that feeds the crystal-containing slurry to the hydraulic wash column; and a unit that melts crystals in a circulation slurry discharged through the discharging port.

In the purification apparatus of the present invention including not only a pipe that feeds a crystal-containing slurry to the hydraulic wash column but also a nozzle at an introduction port that introduces a liquid to the hydraulic wash column (the nozzle is other than a nozzle at the return port and a pipe that feeds the crystal-containing slurry to the hydraulic wash column), stagnation of the liquid in and around the nozzle can be prevented and freezing thereof can be prevented.

Preferably, in the purification apparatus of the present invention, the nozzle at the introduction port is at least one selected from the group consisting of an instrumentation nozzle, a sampling nozzle, a pressure control valve nozzle, a pipe insert nozzle, and an emergency injection nozzle.

Preferably, in the purification apparatus of the present invention, the nozzle at the introduction port is located in an upper face in the hydraulic wash column.

The upper face in the hydraulic wash column is likely to have low temperature. In response, the nozzle at the introduction port is provided in the upper face in the hydraulic wash column, and thus, significantly, stagnation of the liquid in and around the nozzle can be prevented and freezing thereof can be prevented.

The upper face is not limited as long as it is an upper face inside the hydraulic wash column. For example, the upper face may be a face that faces the surface of the crystal bed formed in the hydraulic wash column.

In particular, the nozzle at the introduction port is more preferably located in the uppermost face of the hydraulic wash column.

The effects of the present invention are significantly achieved when the purification apparatus of the present invention further includes a mother liquor collection chamber in which the discharged mother liquor is collected; and the nozzle at the introduction port penetrates the mother liquor collection chamber, and is connected to a crystallization chamber to which the crystal-containing slurry in the hydraulic wash column is fed.

As described above, the mother liquor collection chamber is usually located in the top portion of the hydraulic wash column. When the nozzle at the introduction port penetrates the mother liquor collection chamber and is connected to the crystallization chamber to which the crystal-containing slurry in the hydraulic wash column is fed, thermally insulating the nozzle penetrating the mother liquor collection chamber or controlling the temperature thereof is difficult. According to the embodiments of the present invention, significantly, stagnation of the liquid in and around the nozzle can be prevented and freezing can be prevented.

Preferably, the purification apparatus of the present invention further includes a line that transports the discharged mother liquor, and is connected to the nozzle at the introduction port. Specifically, preferably, a forward side of the nozzle at the introduction port is a port for introducing the liquid into the hydraulic wash column, and a backward side of the nozzle at the introduction port is connected to the line that transports the mother liquor. As a result, the discharged mother liquor can be effectively used and the effects of the present invention can be achieved.

The line that transports the mother liquor and the pipe that transports the mother liquor constitute a part of the circulation path for the discharged mother liquor. In other words, the nozzle at the introduction port is connected to the circulation path for the discharged mother liquor.

Preferably, in the purification apparatus of the present invention, the line that transports the mother liquor includes a heating mechanism.

Preferred examples of the heating mechanism include: a mechanism including a heater through which the mother liquor is passed and heated in the path of the line that transports the mother liquor; a mechanism directly heating the line that transports the mother liquor so that the mother liquor passing through the line is heated; and a mechanism using both of these mechanisms. Examples of the heater include a vertical multitubular heat exchanger, a horizontal multitubular heat exchanger, a double pipe heat exchanger, a spiral heat exchanger, and a plate heat exchanger. An example of the mechanism directly heating the line that transports the mother liquor so that the mother liquor passing through the line is heated is a mechanism including around the line an electric heater, a steam trace system, a hot water trace system, a steam jacket, a hot water jacket, or the like. The whole or part of the line may be directly heated.

The heating temperature of the heating mechanism may be set to an appropriate temperature according to the melting point of the compound, and can be appropriately adjusted within the range of 10° C. to 100° C., for example.

For example, when the compound is (meth)acrylic acid, the heating temperature by the heating mechanism is preferably 15° C. or higher, more preferably 18° C. or higher. The heating temperature is preferably 50° C. or lower, more preferably 40° C. or lower.

The heating temperature by the heating mechanism is the heating temperature in the heating mechanism. When the heating is performed by feeding a heating medium to the heating mechanism, the heating temperature is the temperature of the heating medium.

The heating duration by the heating mechanism may be appropriately determined.

The hydraulic wash column in the purification apparatus of the present invention may have any dimensions. Preferably, the inner diameter of the column (the crystallization chamber) is 30 to 2000 mm, for example. The height of the column is preferably 1000 to 15000 mm.

The filter that filters the crystal-containing slurry in the hydraulic wash column in the present invention may have any dimensions. Preferably, the inner diameter of the filter is 10 to 30 mm, for example. The height of the filter is preferably 20 to 300 mm.

The filter may be provided with a large number of circular holes, slits (notches), or rectangular holes, for example. The filter may have the same shape as the pipe, such as a cylindrical shape, but is not limited thereto.

When the filter is provided with circular holes, the diameter of each hole may be appropriately adjusted depending on the size of the crystals, and is preferably 50 to 500 μm, for example. The number of holes is not limited, and may be adjusted according to the pressure loss, for example.

The pipe that is connected to the filter and transports a mother liquor is usually located above the filter.

The number of pipes that are connected to the filter and transports a mother liquor is not limited. For example, in an industrial-scale hydraulic wash column, 50 to 350 pipes are preferably connected in parallel per square meter of the cross-sectional area of the hydraulic wash column.

The filter and the pipe that is connected to the filter and transports a mother liquor are as described for the production method of the present invention.

The purification apparatus of the present invention may further include a mechanism that heats an outer wall surface of the hydraulic wash column.

Non-limiting examples of the mechanism that heats the outer wall surface of the hydraulic wash column include heating mediums and known heaters. For example, part of the hydraulic wash column may be heated with a heating medium or the like, or substantially the entire hydraulic wash column may be heated (jacket heating).

When the heating mechanism is of jacket heating, for example, the jacket may be made of any material such as metal (e.g., stainless steel or carbon steel) or resin.

The outside of the jacket may be provided with a heat insulating material, a tracing system, and the like.

The structure of the jacket is not limited.

The inside of the jacket may be provided with any structure such as a structure that promotes heat transfer, such as a baffle.

The jacket preferably has an average thickness (the width of the space where the heating medium flows) of 5 to 200 mm, for example.

The heat flux through the wall of the hydraulic wash column from the jacket is preferably more than 100 W/m², more preferably more than 200 W/m², still more preferably more than 500 W/m².

The upper limit of the heat flux through the wall of the hydraulic wash column from the jacket is usually 4000 W/m² or less, but is not limited thereto.

A side wall of the jacket may be provided with a sight glass (an observation window) or a hand hole (a hole for putting a hand inside during maintenance). In these cases, they can be covered with a cover. The numbers of sight glasses and hand holes to be provided are not limited.

Non-limiting examples of the heating medium include water, antifreeze, a methanol water mixture (an aqueous methanol solution), and gas. The heating medium may be appropriately selected in consideration of the freezing point of the compound to be purified, for example.

The number of pipes that feed the crystal-containing slurry to the hydraulic wash column and the number of feed nozzles (slurry feed ports) that may be connected to the tips of the pipes are not limited. Each of the numbers may be one or more (FIG. 1 shows the case where the number of pipes that feed the crystal-containing slurry to the hydraulic wash column is one).

The feed nozzle may have, at its tip, a distribution mechanism that distributes the slurry.

The hydraulic wash column may further include a dispersing chamber and a central displacer body (see JP 2005-509010 T).

The body or the periphery of the hydraulic wash column may be provided with instrumentation equipment such as a thermometer (e.g., a multi-point thermometer), a pressure gauge, or an interface level meter (e.g., an optical interface level meter).

The hydraulic wash column itself may be placed in a temperature-controlled casing (including a large casing such as a building).

Preferably, the purification apparatus of the present invention further includes: a discharging line that connects the discharging port for a crystal-containing circulation slurry in the hydraulic wash column and the melting unit; and a return line that connects the melting unit and the return port of the hydraulic wash column. During use of the purification apparatus of the present invention, the circulation slurry or the circulation liquid containing a melt is circulated in the discharging line and the return line. As described above, herein, the circulation path is also referred to as a melt loop.

The purification apparatus of the present invention preferably includes a mechanism that discharges crystals from a crystal bed in the hydraulic wash column.

Non-limiting examples of the mechanism that discharges crystals from a crystal bed include a rotor blade or scraper described in JP 2005-509009 T and a mechanism using liquid dynamic pressure described in EP 1469926. One or more of these may be used. When the rotor blade or scraper is used, the rotation speed is preferably 20 to 60 rpm. The material of the rotor blade or scraper is preferably metal such as stainless steel.

The melting unit is usually a heater. Examples of the heater include those having a structure that efficiently transfers heat to the crystal-containing slurry, such as a vertical multitubular heat exchanger, a horizontal multitubular heat exchanger, a double pipe heat exchanger, a spiral heat exchanger, a plate heat exchanger, or an electric heater. Preferably, the heater is provided in the melt loop and the circulation slurry and the circulation liquid after the melting step are circulated in the forced circulation system in which the circulation slurry is circulated by a pump provided in the melt loop.

The purification apparatus of the present invention may include a mechanism (return mechanism) that returns a portion of the circulation liquid containing the melt obtained in the crystal melting unit to the hydraulic wash column.

The return mechanism may be any mechanism that is used to return a portion of the circulation liquid separated from the other portion of the circulation liquid to the hydraulic wash column. For example, when a product discharging line that is connected to a product discharging port is branched from the return line that connects the melting unit and the return port, this branched line portion corresponds to the return mechanism. For example, the branched line portion may be a T-junction.

In particular, the return mechanism preferably returns a portion of the circulation liquid containing the melt obtained in the crystal melting unit to the hydraulic wash column so that at least a portion of the returned circulation liquid serves as a washing liquid for crystals.

The return port is preferably provided at the bottom of the hydraulic wash column so that the circulation liquid can be returned upward. The return mechanism may be, for example, a combination of the branched line portion and the return port at the bottom of the hydraulic wash column.

The purification apparatus of the present invention may further include the mechanism that controls the amount of the circulation liquid to be returned.

The purification apparatus of the present invention further including the mechanism that controls the amount of the circulation liquid to be returned (control mechanism) can adjust the amount of the circulation liquid to be returned, for example, and if needed, can efficiently separate impurities. Thereby, a product can be efficiently obtained.

An example of the control mechanism is a valve installed in the line of the return mechanism (branched line portion).

The control mechanism may directly or indirectly control the amount of the circulation liquid to be returned.

When the control mechanism directly controls the amount of the circulation liquid to be returned, the control mechanism may be a valve (not shown) installed in the return line 24 shown in FIG. 1, for example.

A valve may be installed in both the product discharging line 23 and the return line 24.

Further, flowmeters may be installed in the feed line 11 (including the pipe 4) that feeds the crystal-containing slurry 11a to the hydraulic wash column, the product discharging line 23, and the return line 24 to measure the flow rates, and the flow rates may be appropriately adjusted by controlling the valves in accordance with the measured flow rates. The valves can be controlled according to the flow rates in the product discharging line 23 and the return line 24. Furthermore, the valves may be controlled according to the temperature in the hydraulic wash column measured with a multi-point thermometer attached thereto.

Preferably, the purification apparatus of the present invention further includes a product discharging port. For example, more preferably, the purification apparatus of the present invention further includes: the product discharging line branched from the return line that connects the melting unit and the return port; and the product discharging port connected to the product discharging line.

FIG. 1 shows an example of the purification apparatus of the present invention. The crystal-containing slurry 11a is fed into the crystallization chamber 15 of the hydraulic wash column 1 through the feed line 11 (including the pipe 4) that feeds the crystal-containing slurry to the hydraulic wash column, and the crystals deposit at the lower part of the crystallization chamber 15 to form a crystal bed (not shown). The crystal-containing slurry in the crystallization chamber 15 of the hydraulic wash column 1 is filtered using the filter 2; a mother liquor (filtrate) is discharged using the pipe 3 that is connected to the filter 2 and collected in the collection chamber 14; and a portion of the mother liquor is transported through the mother liquor transport lines 16a and 16b, heated with the heaters 17a and 17b, and then introduced into the instrumentation nozzle 13a and the pressure control valve nozzle 13b. The remaining mother liquor can be transported through the line 18, mixed with the crystal-containing slurry 11a, and fed to the hydraulic wash column as a crystal-containing slurry.

The crystals are discharged from the bottom of the hydraulic wash column 1 together with a circulation liquid circulated in a melt loop that passes through the bottom of the crystallization chamber 15 of the hydraulic wash column 1 as a crystal-containing slurry. The slurry passes through the discharging line 21 that connects the crystal discharging port 20 and the melting unit 22 and is transported to the melting unit 22. A portion of the melt obtained by melting the crystals in the melting unit 22 is returned into the crystallization chamber 15 of the hydraulic wash column 1 through the return line 24 that connects the melting unit 22 and the return port 25. At least a portion of the rest of the melt is discharged from the purification apparatus as the purified product 23a through the product discharging line 23 that is branched from the return line 24 and connected to the product discharging port.

Method for Using Purification Apparatus

The present invention also relates to a method for using a purification apparatus including a step of purifying a compound using the purification apparatus of the present invention.

EXAMPLES

The present invention will be described in more detail below with reference to examples, but the present invention is not limited by the following examples, and appropriate modifications may be made within the scope that can conform to the gist of the above and later descriptions. All of them are included in the technical scope of the present invention.

Unless otherwise specified, "%" indicates "% by mass" and "parts" indicates "parts by mass."

Method for Preparing Acrylic Acid Aqueous Solution

An acrylic acid aqueous solution was prepared according to the method described in WO 2010/032665 as follows: propylene was catalytically oxidized in gas phase to obtain an acrylic acid-containing gas; and the acrylic acid-containing gas was treated in an absorption tower.

Method for Preparing Feed Slurry

The acrylic acid aqueous solution was fed to a crystallization vessel having a heat transfer area of $1.4 \text{ m}^2$. A cooling medium was fed to a jacket provided around the wall of the crystallization vessel for indirect cooling. Crystals adhering to the inner surface of the crystallization vessel were scraped off with a scraper installed in the crystallization vessel. Thus, a crystal-containing slurry (feed slurry) was prepared.

Purification apparatus

A purification apparatus used includes the following units and is similar to the purification apparatus shown in FIG. 1, except for the number of filters 2 and the number of mother liquor discharging pipes 3.

Hydraulic wash column 1: inner diameter 60 mm; height 2000 mm

Filter 2: inner diameter 25 mm; length (height) 200 mm; number of filters 1; material PEEK; structure of filter: circular holes with a diameter of 250 μm Pipe 3 that is connected to the filter 2 and transports a mother liquor: inner diameter 25 mm; length 1600 mm; number of pipes 1; material stainless steel Return of circulation liquid into the hydraulic wash column 1: upward return from the bottom of the column through the return port 25

Structure of jacket: provided to the entire apparatus (not shown)

Pipe 4 that feeds the crystal-containing slurry 11a into the hydraulic wash column 1, inner diameter: 25 mm; number of pipes 1

Inner diameter of the melt loop line (discharging port 20, discharging line 21, product discharging line 23, return line 24, return port 25) such as a crystal discharging line: 25 mm Melting unit 22: double pipe heat exchanger

A flow control valve (not shown) was installed in the product discharging line 23 in the melt loop.

Method for Operating Purification Apparatus

The purification apparatus was operated in the following way.

A slurry containing acrylic acid crystals (feed slurry) was fed to the hydraulic wash column prepared as above under the conditions of a slurry concentration (crystal concentration) of 10% by mass, a slurry temperature of 10.5° C., and a flow rate of 220 kg/h. The operating internal pressure of the hydraulic wash column was set at 0.4 MPa. A heating medium was introduced into the jacket.

The crystals were discharged together with the circulation liquid through the discharging port 20 of the hydraulic wash column 1 with a scraper at the bottom of the column and were sent as a circulation slurry to a heater (double pipe heat exchanger), which was a melting unit, at a flow rate of 220 kg/h.

The temperature of the heating medium in the double pipe heat exchanger was set at 30° C. The temperature of the liquid (circulation liquid) at the outlet of the heater was 20° C. While a portion of the circulation liquid was discharged as a product through the product discharging line 23, the rest of the circulation liquid was returned to the hydraulic wash column.

Example 1

A mother liquor was discharged from the hydraulic wash column at a flow rate of 204.8 kg/h through a mother liquor discharging pipe. The mother liquor immediately after being discharged had a temperature of 10° C.

The discharged mother liquor was collected in a mother liquor collection chamber 14; a portion of the mother liquor was transported through a mother liquor transport line 16a, heated with a double pipe heater 17a, introduced into an instrumentation nozzle 13a at a rate of 35 kg/h at 16° C., and introduced into a crystallization chamber 15 of a hydraulic wash column 1 through an instrumentation nozzle 13a equipped with a pressure gauge. Separately, a portion of the collected mother liquor was transported through a mother liquor transfer line 16b, heated with a double pipe heater 17b, introduced into a pressure control valve nozzle 13b at a rate of 35 kg/h at 16° C., and introduced into the crystallization chamber 15 of the hydraulic wash column 1 through a pressure control valve nozzle 13b. The remaining mother liquor was transported through a line 18, mixed with the crystal-containing slurry 11a, and fed as a crystal-containing slurry to the hydraulic wash column.

As a result, stable operation can be achieved without freezing of the nozzles.

Comparative Example 1

Acrylic acid as a product was obtained as in Example 1, except that the discharged mother liquor was not returned to the instrumentation nozzle 13a and the pressure control valve nozzle 13b, but was all recirculated as a portion of the feed slurry.

The nozzles froze, and the pressure gauge gave an erroneous indication, failing to monitor the operating conditions correctly. As a result, the apparatus was stopped to solve the freezing.

Comparative Example 2

Acrylic acid as a product was obtained as in Example 1, except that the discharged mother liquor was not heated with the double pipe heater when it was introduced into the crystallization chamber 15 of the hydraulic wash column 1 through the instrumentation nozzle 13a and the pressure control valve nozzle 13b. The mother liquor before being introduced into each nozzle had a temperature of 8° C.

The nozzles froze, and the pressure gauge gave an erroneous indication, failing to monitor the operating conditions correctly. As a result, the apparatus was stopped to solve the freezing.

These results demonstrate that a high-quality product can be obtained safely and stably by the method for producing a compound, the method including: a step of feeding a slurry containing crystals of the compound to a hydraulic wash column; a step of melting crystals in a crystal-containing circulation slurry discharged from the hydraulic wash column; a step of discharging a mother liquor using a filter from the crystal-containing slurry in the hydraulic wash column; and a step of introducing a liquid having a temperature equal to or higher than the temperature of the mother liquor immediately after being discharged in the mother liquor discharging step into a nozzle attached to the hydraulic wash column from outside the hydraulic wash column, the nozzle being other than a nozzle at a return port for a circulation liquid containing a melt obtained in the melting step and a pipe that feeds the crystal-containing slurry to the hydraulic wash column.

REFERENCE SIGNS LIST

1 hydraulic wash column
2 filter that filters crystal-containing slurry in crystallization chamber of hydraulic wash column
3 pipe that is connected to filter and transports mother liquor
4 pipe that feeds crystal-containing slurry to crystallization chamber of hydraulic wash column
11 feed line (that feeds crystal-containing slurry to crystallization chamber of hydraulic wash column)
11a crystal-containing slurry
13a (instrumentation) nozzle
13b (pressure control valve) nozzle
14 mother liquor collection chamber
15 crystallization chamber
16a, 16b lines that transport mother liquor
17a, 17b heater
18 line
19 pressure control line
20 circulation slurry discharging port
21 discharging line that connects discharging port for circulation slurry and melting unit
22 melting unit
23 product discharging line (connected to product discharging port)
23a (purified) product
24 return line (that connects melting unit and return port)
25 return port (for circulation liquid containing melt of discharged crystals)
P1, P2 pump

The invention claimed is:
1. A method for producing a compound, the method comprising:
    a step of feeding a slurry containing crystals of the compound to a hydraulic wash column;
    a step of melting crystals in a crystal-containing circulation slurry discharged from the hydraulic wash column;

a step of discharging a mother liquor using a filter from the crystal-containing slurry in the hydraulic wash column; and a step of introducing a liquid having a temperature equal to or higher than the temperature of the mother liquor immediately after being discharged in the mother liquor discharging step into a nozzle attached to the hydraulic wash column from outside the hydraulic wash column, the nozzle being other than a nozzle at a return port for a circulation liquid containing a melt obtained in the melting step and a pipe that feeds the crystal-containing slurry to the hydraulic wash column;

wherein the nozzle attached to the hydraulic wash column is at least one selected from the group consisting of an instrumentation nozzle, a sampling nozzle, a pressure control valve nozzle, a pipe insert nozzle, and an emergency injection nozzle.

2. The method for producing a compound according to claim 1, wherein the liquid having a temperature equal to or higher than the temperature of the mother liquor contains at least one of the compound or water.

3. The method for producing a compound according to claim 1, wherein the liquid having a temperature equal to or higher than the temperature of the mother liquor contains at least a portion of the mother liquor discharged in the mother liquor discharging step.

4. The method for producing a compound according to claim 1, wherein the liquid having a temperature equal to or higher than the temperature of the mother liquor contains at least a portion of the mother liquor discharged in the mother liquor discharging step, the portion of the mother liquor having been heated.

5. The method for producing a compound according to claim 1, wherein the nozzle attached to the hydraulic wash column penetrates a mother liquor collection chamber in which the mother liquor discharged in the mother liquor discharging step is collected, and is connected to a crystallization chamber to which the crystal-containing slurry in the hydraulic wash column is fed.

6. The method for producing a compound according to claim 1, further comprising:

a step of preparing the slurry containing crystals of the compound from a compound-containing solution.

7. The method for producing a compound according to claim 6, wherein the compound-containing solution is a (meth) acrylic acid aqueous solution or a crude (meth) acrylic acid solution.

8. The method for producing a compound according to claim 1, further comprising:

a step of preparing the compound-containing solution from a raw material.

9. The method for producing a compound according to claim 8, wherein the raw material is at least one selected from the group consisting of propane, propylene, acrolein, isobutene, methacrolein, acetic acid, lactic acid, isopropanol, 1,3-propanediol, glycerol, and 3-hydroxypropionic acid.

10. A method for purifying a compound, the method comprising:

a step of feeding a slurry containing crystals of the compound to a hydraulic wash column;

a step of melting crystals in a crystal-containing circulation slurry discharged from the hydraulic wash column;

a step of discharging a mother liquor using a filter from the crystal-containing slurry in the hydraulic wash column; and a step of introducing a liquid having a temperature equal to or higher than the temperature of the mother liquor immediately after being discharged in the mother liquor discharging step into a nozzle attached to the hydraulic wash column from outside the hydraulic wash column, the nozzle being other than a nozzle at a return port for a circulation liquid containing a melt obtained in the melting step and a pipe that feeds the crystal-containing slurry to the hydraulic wash column;

wherein the nozzle attached to the hydraulic wash column is at least one selected from the group consisting of an instrumentation nozzle, a sampling nozzle, a pressure control valve nozzle, a pipe insert nozzle, and an emergency injection nozzle.

11. A purification apparatus that purifies crystals, the purification apparatus comprising:

a hydraulic wash column that includes a discharging port for a crystal-containing circulation slurry and a return port for a circulation liquid containing a melt of discharged crystals;

a pipe that feeds a crystal-containing slurry to the hydraulic wash column;

a filter that discharges a mother liquor from the crystal-containing slurry in the hydraulic wash column;

a pipe that is connected to the filter and transports the mother liquor;

a nozzle at an introduction port that introduces a liquid to the hydraulic wash column, the nozzle being other than a nozzle at the return port and a pipe that feeds the crystal-containing slurry to the hydraulic wash column, and is at least one is at least one selected from the group consisting of an instrumentation nozzle, a sampling nozzle, a pressure control valve nozzle, a pipe insert nozzle, and an emergency injection nozzle; and a unit that melts crystals in a circulation slurry discharged through the discharging port.

12. The purification apparatus according to claim 11, wherein the nozzle at the introduction port is located in an upper face in the hydraulic wash column.

13. The purification apparatus according to claim 11, further comprising a mother liquor collection chamber in which the discharged mother liquor is collected, wherein the nozzle at the introduction port penetrates the mother liquor collection chamber, and is connected to a crystallization chamber to which the crystal-containing slurry in the hydraulic wash column is fed.

14. The purification apparatus according to claim 11, further comprising:

a line that transports the discharged mother liquor, and is connected to the nozzle at the introduction port.

15. The purification apparatus according to claim 14, wherein the line that transports the mother liquor comprises a heating mechanism.

16. The method for producing a compound according to claim 1, wherein the nozzle attached to the hydraulic wash column is located in an upper face in the hydraulic wash column.

17. The method for purifying a compound according to claim 10, wherein the nozzle attached to the hydraulic wash column
   is located in an upper face in the hydraulic wash
   column.

<div align="center">* * * * *</div>